US006468580B1

(12) United States Patent
Choi et al.

(10) Patent No.: US 6,468,580 B1
(45) Date of Patent: Oct. 22, 2002

(54) PROCESS FOR THE PRODUCTION AND USE OF LYSINE BASE DRY POWDERS

(75) Inventors: Jong Soo Choi, Seoul; Tae Hui Kim, Jeonbuk; Sung Hyeon Kim, Jeonbuk; Yun Su Du, Jeonbuk, all of (KR); Ulrich Eidelsburger, Meckenheim; Joachim Meyer, Maxdorf, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/602,320

(22) Filed: Jun. 23, 2000

(30) Foreign Application Priority Data

Jul. 12, 1999 (DE) .......................................... 19932059

(51) Int. Cl.⁷ .............................. A23K 1/16; A23J 3/20
(52) U.S. Cl. ........................................ 426/656; 426/807
(58) Field of Search ................................. 426/626, 807

(56) References Cited

U.S. PATENT DOCUMENTS 4,701,328 A  10/1987  Bercovici et al. .............. 426/2
4,919,945 A   4/1990  Spindler et al. ............... 426/69
5,990,350 A * 11/1999  Stevens et al. ............. 562/562

FOREIGN PATENT DOCUMENTS

| DE | 24 47 274 | 4/1975 |
| EP | 122 163 | 10/1984 |
| EP | 337 440 | 10/1989 |
| EP | 457 075 | 11/1991 |
| EP | 497 177 | 8/1992 |
| EP | 533 039 | 3/1993 |
| EP | 923 878 | 6/1999 |
| GB | 1 456 923 | 12/1976 |

* cited by examiner

*Primary Examiner*—Chhaya D. Sayala
(74) *Attorney, Agent, or Firm*—Keil & Weinkauf

(57) ABSTRACT

The invention relates to a feedstuff or premix comprising lysine base dry powder, where the free lysine base content of the dry matter is more than 70% by weight, and to a process for producing lysine base dry powder and its use.

8 Claims, No Drawings

PROCESS FOR THE PRODUCTION AND USE OF LYSINE BASE DRY POWDERS

The invention relates to the use of lysine base dry powders in foodstuffs, pharmaceutical preparations and animal feeds and to a process for their production.

L-lysine is, as an essential amino acid, widely used as addition in foodstuffs and feedstuffs, for example for producing dietetic human food products and feedstuffs. Amino acids such as lysine are also widely used in medicine, for example as constituent of infusion solutions. L-lysine promotes, for example, the growth of bone and stimulates cell division and nucleoside synthesis.

More than 90% of the L-lysine synthesized around the world is used to produce feedstuffs, specifically for producing pig or poultry feed. L-lysine is used to produce the feed in order to supply the requirements of the livestock for the essential amino acid which is deficient in the usual protein sources used in livestock nutrition. Lysine in the feed abolishes the limitation, and the zootechnical performance of the livestock can be markedly enhanced.

To date it has mainly been L-lysine monohydrochloride (L-lysine HCl) with an L-lysine content of about 79% which has been employed for L-lysine supplementation of feedstuffs, for example. The use of lysine hydrochloride results in an increased water intake by the livestock (U.S. Pat. No. 4,919,945). This may very often lead to the unwanted "wet litter" and thus to an increased risk of infection for the livestock. In order to obtain a less hygroscopic product it has been necessary to mix a large amount of additives into the concentrate. However, this reduced even further the content of the amino acid which is in many cases already relatively low.

In addition, basic amino acids in the form of their chloride salts have a very bitter taste which, with larger supplements in the feed, results in a reduced nutrient intake by the livestock.

The use of L-lysine hydrochloride in infusion solutions in medicine may lead to a hyperchloremic metabolic acidosis. The use of such infusion solutions in patients suffering from renal failure results in an unwanted further burden on the already disturbed electrolyte balance of the patient due to the chloride ions.

It is possible in a prior art process (EP-B 122 163) on maintenance of very specific fermentation conditions to obtain a crude fermentation broth which can be dried to a stable solid product. This product obtainable by dehydrating the entire fermentation broth has, however, an L-lysine content of only 35 to 48% by weight which is, accordingly, distinctly less than that of L-lysine monohydrochloride.

EP-B 533 039 claims an animal feed supplement which has a high content of an "amino acid" and which still contains most of the constituents of the fermentation broth. The final products obtained in the disclosed fermentation process (see examples) are not the free amino acids but the acids in the form of their salts, e.g. as sulfates or carbonates, as is evident from the fermentation conditions.

The fermentation broth is spray dried without further purification. The percentages by weight of amino acid, e.g. of L-lysine base, stated in the patent thus only comprise a value for free base theoretically calculated on the basis of the lysine salt.

Another product form which is produced is a liquid lysine base which, besides 50% lysine base, contains fermentation by-products and, principally, water. Besides high costs for transport, storage, packaging and handling because of the large total volume, liquid lysine base has the disadvantage that it requires special application techniques and, once again, the required product concentration is low on production.

Many lysine forms are described as having a product-intrinsic stickiness in the dried state, and the prior art describes particular additions, for example $CaSO_4$, for reducing this (DE-A 2447274).

It is an object of the present invention to provide an L-lysine base dry powder which has a high content of free L-lysine and which has a large nutritional effect, and a process for its production. It was intended that the solid final product have good storage and processing properties. In addition, the product ought to have little stickiness so that no additions are made to reduce it, which would unnecessarily diminish the required product concentration.

We have found that this object is achieved by a feedstuff or premix comprising lysine base dry powder wherein the free lysine base content of the dry matter is more than 70% by weight.

The product can be used comparably to lysine salts (e.g. hydrochloride) and has excellent flow properties and little stickiness. It can also be used to produce a concentrated lysine base solution by dissolving in water.

The product normally has a residual water content of about 2 to 3% by weight.

The free lysine base content of the dry matter is more than 70% by weight, preferably more than 90% by weight.

Sources of lysine for producing L-lysine base dry powders are, for example, proteins from which L-lysine can be obtained by acid hydrolysis. D,L-lysine is obtainable by chemical synthesis, for example from D,L-α-amino-ε-caprolactam, and L-lysine and D-lysine can also be obtained by subsequent racemate resolution.

L-lysine is normally obtained by a fermentation process using microorganisms essentially of the genera Corynebacterium, Brevibacterium, Arthrobacter, Microbacterium, Bacillus or Nocardia and a subsequent purification, preferably on an ion exchanger. This may involve the fermentation broth being put on the ion exchanger directly or after removal of the biomass. Microbiological processes for producing L-lysine are described, for example, in *Trends in Biotechnology* 1983, 1, 70–74.

The novel process is distinguished by the free lysine base content of the dry matter being more than 70% by weight, preferably more than 90% by weight.

The novel lysine base dry powders were then converted into powder form by conventional concentration and/or drying processes such as, for example, spray drying, fluidized spray drying, drum drying or freeze drying. The preferred drying process is spray drying (EP-A 0 457 075; EP-A-0 497 177), in which case the temperature is from 80 to 200° C., preferably 110 to 170° C.

The term lysine base refers to lysine, preferably L-lysine, in the form of the free base ($H_2N$—$(CH_2)_4$—$CHNH_2$—$CO_2H$; pK~10.5). Besides the content of free lysine base (70 to 97% by weight), the dry matter may also comprise small contents of other amino acids or proteins from the fermentation medium.

The lysine base dry powders are advantageously employed in the novel use in foodstuffs, preferably in livestock nutrition, particularly preferably as addition in feed for pigs, piglets and poultry such as, for example, layers, broilers or turkeys. For this purpose they can be added to all conventional livestock feeds such as compound feeds and/or single-component feeds such as cereals such as wheat, oats, rye, barley and legumes, corn or corncob mix. The lysine base dry powder can be added to the feedstuffs directly or in the form of premixes in which they have been mixed with other feed additives before use.

Auxiliaries which can be added to the lysine base dry powders are all auxiliaries customary in agriculture, such as flavorings, colorings, appetite stimulants, antibiotics, probiotics and/or enzymes. The auxiliaries are advantageously added in an amount of from 0.1% to 50% of the weight of the lysine base dry powders, preferably in an amount of from 0.1 to 10% of the weight.

Different amounts of the lysine base dry powders are advantageously used depending on the composition of the feedstuff. It is normally sufficient to add from 0.1 to 10 kg per metric ton of livestock feed for lysine supplementation. Lysine bases are preferably added in amounts of from 0.5 to 5 kg per metric ton of livestock feed.

The lysine base dry powders can be used to produce the feedstuffs or mixtures thereof in a manner known per se. Addition to the feedstuff can take place immediately after harvest or after storage. The solid or liquid lysine base can be added to the feedstuff directly or in the form of premixes, advantageously during the pelleting or extrusion of the feed, for example through a metering device.

The lysine base dry powders can also be used in pharmaceutical or cosmetic preparations.

A further use of the novel lysine base dry powder is for the industrial synthesis of polylysine.

The following examples are intended to illustrate the invention in detail:

EXAMPLE 1

L-lysine Production by Fermentation

After a conventional lysine fermentation (72 h) with Corynebacterium glutamicum ATCC 21526 as described in U.S. Pat. No. 3,708,395, the fermentation broth was acidified to pH 2 with $H_2SO_4$, eluted through an ion exchanger with $NH_3$, freed of $NH_3$ in vacuo, and concentrated to 68% dry matter. This concentrate was used for the spray drying.

EXAMPLE 2

L-lysine Spray Drying

The concentrate from Example 1 was spray dried under the following conditions:

spray drier with atomizer entry temperature 165° C.

exit temperature 110° C.

atomizer speed 10,000 rpm (spray dryer: Niro Production minor)

The product dried in this way contained 97% dry matter and a lysine base content of 91.8%. It was not sticky and was easy to process.

EXAMPLE 3

Lysine Base Feeding Trial on the Efficacy of 90% Lysine Base in Piglet Rearing

The intention of this trial with weaners was to test the product 90% lysine base for its efficacy by comparison with Sewon L-lysine HCl 99% feed (79% L-lysine). The trial product is a spray-dried lysine base with an active substance content of 90% L-lysine.

A total of 45 piglets (GLxP) with an age of 28 days and an average weight of 7.2 kg were used for the 49-day feeding trial. The animals were derived from 9 litters and were distributed at random to the 5 treatments on the block-formation principle. The following trial variants were tested:

| Group | Lysine supplement % | Test substance % |
|---|---|---|
| I | — | — |
| II | 0.12 | 0.152% L-lysine HCl |
| III | 0.24 | 0.304% L-lysine HCl |
| IV | 0.12 | 0.133% 90% lysine base |
| V | 0.24 | 0.266% 90% lysine base |

Group I served as negative control and received the basic feed without lysine supplement. In groups II and III respectively, 0.12 and 0.24% lysine in the form of the commercial product Sewon L-lysine HCl 99% feed (min. 79% L-lysine, marketed by BASF Aktiengesellschaft Ludwigshafen) was added to the basic feed. In groups IV and V respectively, the supplementation was with the corresponding lysine equivalents in the form of the test substance 90% lysine base. The composition of the low-lysine basic feed used is to be found in Table 1. The basic feed contained 0.79% lysine and was intended to cover about 60% of the piglets' lysine requirements. All the other amino acid contents covered requirements. With the exception of lysine, the feed complied with the requirements for piglet rearing feed of standard type II.

The stock were kept in individual pens in an air-conditioned trial house. The room temperature was lowered continuously during the trial from 26° C. to 22° C., the relative humidity being about 55%. The pelleted feed was provided ad libitum. Unconsumed feed was reweighed twice a week. The weight of the stock was determined weekly. The trial parameters were the weight gain, feed consumption and feed conversion.

The trial data were subjected to analysis of variance and tested for significance in the F test, and the averages for the individual groups were compared by the Student/Newman-Keuls test. Significant differences between the group averages are indicated by different superscripts.

The results for the weight change, daily gains, feed consumption and feed conversion are compiled in Table 2. The weight change, feed consumption and feed conversion for the stock in group I were significantly worse than for the stock in groups II–V supplemented with the lysine products. Accordingly, the supply of lysine in the basic feed was distinctly deficient.

Supplementation with 0.12% and 0.24% lysine in the form of lysine HCl significantly increased the daily gain from 209 g/d to, respectively, 312 and 349 g, corresponding to 49% and 67% relative to group I. The corresponding addition of lysine in the form of lysine base improved the daily gain to, respectively, 308 and 355 g, i.e. by 47% and 70% compared with the negative control (group I). The increase in growth was thus comparable with both lysine supplements with both lysine products.

The feed consumption was likewise significantly influenced by the increasing supply of lysine. On addition of 0.12% and 0.24% lysine in the form of lysine HCl the feed consumed by the piglets was demonstrably increased by 27% and 30%, respectively, compared with the animals in the control group. The animals in groups IV and V with a corresponding lysine base supplementation showed a feed consumption which was 25% and 33%, respectively, higher than in group I. Thus, there was a comparable increase in the feed consumption with the two lysine forms, which also suggests that acceptance of the lysine base was good.

The feed conversion was significantly improved by 15% and 22%, respectively, over the negative control by the addition of 0.12% and 0.24% lysine in the form of lysine HCl and lysine base. The effect of the level of supplementation was also verified for the two lysine forms. The two lysine products accordingly show comparable efficacy in the feed conversion.

This trial revealed that the biological efficacy for the trial product 90% lysine base was comparable to that for the standard product lysine HCl when comparison was based on equal amounts of lysine supplementation. This applies to all zootechnical parameters investigated: the daily gains, feed consumption and feed conversion. It can be concluded from the results that the newly developed product 90% lysine base is at least as effective as the standard product lysine HCl.

TABLE 1

Composition of the basic feed used

| Components | % |
|---|---|
| Wheat | 40.00 |
| Corn | 18.12 |
| Barley | 6.00 |
| Extracted soybean meal | 14,15 |
| Corn gluten | 10.00 |
| Meat/bone meal | 3.00 |
| Wheat | 2.10 |
| Alfalfa meal | 2.00 |
| Soybean oil | 2.00 |
| DL-methionine | 0.05 |
| L-threonine | 0.08 |
| Mineral, vitamin and trace element supplement | 2.50 |
| Crude protein | 17.70 |
| Metabolizable energy, MJ/kg | 13.10 |
| Calcium | 0.90 |
| Phosphorus | 0.70 |

TABLE 2

Effect of L-lysine HCl 99% and 90% lysine base on the weight, daily gains, daily feed consumption and feed conversion of weaners

| | Group | | | | |
|---|---|---|---|---|---|
| | I | II | III | IV | V |
| lysine supplement, % | — | 0.12 | 0.24 | 0.12 | 0.24 |
| lysine form | — | lysine HCl | lysine HCl | lysine base | lysine base |
| Initial weight, kg | 7.19 ± 0.92 | 7.21 ± 0.93 | 7.20 ± 0.72 | 7.19 ± 0.72 | 7.20 ± 0.99 |
| Final weight, kg | 18.51b ± 3.98 | 22.50a ± 2.87 | 24.30a ± 3.12 | 22.28a ± 4.16 | 24.59a ± 2.28 |
| relative, % | 100 | 122 | 131 | 120 | 133 |
| Gains, g/d | 209b ± 66 | 312a ± 44 | 349a ± 38 | 308a ± 50 | 355a ± 72 |
| relative, % | 100 | 149 | 167 | 147 | 170 |
| Feed consumption, g/d | 465b ± 121 | 592a ± 83 | 606a ± 64 | 583a ± 107 | 619a ± 99 |
| relative, % | 100 | 127 | 130 | 125 | 133 |
| Feed conversion | 2.23a ± 0.15 | 1.90b ± 0.09 | 1.74c ± 0.11 | 1.89b ± 0.08 | 1.75c ± 0.12 |
| relative, % | 100 | 85 | 78 | 85 | 78 |

We claim:

1. A feedstuff or premix comprising lysine base dry powder, wherein the free lysine base content of the dry matter is 91.8% to 97% by weight.

2. A process for producing lysine base dry powder, which comprises drying a lysine fermentation solution so that the free lysine base content of the dry matter is 91.8% to 97% by weight.

3. The process of claim 2, wherein the lysine fermentation solution is purified, and the purified lysine fermentation solution is then, without neutralization or salt formation, spray dried as free base.

4. The process of claim 3, wherein the lysine fermentation solution is purified on ion exchangers, and the purified lysine fermentation solution is then, without neutralization or salt formation, spray dried as free base.

5. An animal feed or premix containing the spray dried lysine base dry powder produced by the process of claim 4.

6. An animal feed or premix containing the spray-dried lysine base dry powder produced by the process of claim 3.

7. A process for producing lysine base dry powder having a free lysine base content of more than 90% by weight, which comprises purifying a lysine fermentation solution and then, without neutralization or salt formation, spray drying the solution to obtain a free base.

8. The product of the process of claim 7.

* * * * *